United States Patent
He et al.

(10) Patent No.: US 11,643,379 B2
(45) Date of Patent: May 9, 2023

(54) SYNTHESIS OF BRANCHED ALKYL ALCOHOLS BY CU(I)-CATALYZED C-C COUPLING BETWEEN ALKYL GRIGNARD REAGENTS AND ALKYL TOSYLATES

(71) Applicants: Corning Incorporated, Corning, NY (US); Liaoning Shihua University, Fushun (CN)

(72) Inventors: Mingqian He, Horseheads, NY (US); Yang Li, Shanghai (CN); Jing Sun, Fushun (CN); Hongxiang Wang, Shanghai (CN); Mong-dong Zhou, Fushun (CN)

(73) Assignee: CORNING INCORPORATED, Corning, NY (US)

( * ) Notice: Subject to any disclaimer, the term of this patent is extended or adjusted under 35 U.S.C. 154(b) by 127 days.

(21) Appl. No.: 17/209,699

(22) Filed: Mar. 23, 2021

(65) Prior Publication Data
US 2021/0300855 A1    Sep. 30, 2021

(30) Foreign Application Priority Data

Mar. 24, 2020 (CN) .......................... 202010214195.5

(51) Int. Cl.
| | | |
|---|---|---|
| *C07C 29/10* | (2006.01) | |
| *B01J 27/122* | (2006.01) | |
| *C07C 41/30* | (2006.01) | |
| *B01J 31/22* | (2006.01) | |
| *C07C 41/01* | (2006.01) | |
| *C07C 43/164* | (2006.01) | |
| *C07C 29/00* | (2006.01) | |
| *C07C 51/305* | (2006.01) | |

(52) U.S. Cl.
CPC ............. *C07C 29/10* (2013.01); *B01J 27/122* (2013.01); *B01J 31/226* (2013.01); *C07C 29/00* (2013.01); *C07C 41/01* (2013.01); *C07C 41/30* (2013.01); *C07C 43/164* (2013.01); *B01J 2231/4205* (2013.01); *B01J 2531/16* (2013.01); *C07C 51/305* (2013.01)

(58) Field of Classification Search
CPC ....... C07C 29/10; C07C 41/30; C07C 43/164; C07C 31/02; B01J 27/122; B01J 31/226
See application file for complete search history.

(56) References Cited

U.S. PATENT DOCUMENTS

| | | | | |
|---|---|---|---|---|
| 3,493,623 A | * | 2/1970 | Brendel ................ | C11B 9/0015 568/849 |
| 5,728,376 A | | 3/1998 | Attygalle et al. | |
| 2005/0101808 A1 | * | 5/2005 | Ayoub ................... | C07C 29/16 568/909 |

FOREIGN PATENT DOCUMENTS

| | | |
|---|---|---|
| CN | 104974027 A | 10/2015 |
| CN | 108821937 A | 11/2018 |
| JP | 4058249 B2 | 3/2008 |

OTHER PUBLICATIONS

Iwasaki, T., et al., Copper-catalyzed alkyl-alkyl cross-coupling reactions using hydrocarbon additives: Efficiency of catalyst and roles of additives, Journal of Orbanic Chemixtry, vol. 79, No. 18, pp. 8522-8532 (Year: 2014).*

(Continued)

*Primary Examiner* — Yate'K Cutliff

(57) ABSTRACT

A method includes: providing a mixture including at least one alkyl tosylate and a Grignard reagent; and reacting the at least one alkyl tosylate with the Grignard reagent in a C—C coupling reaction mechanism to form a branched aliphatic alcohol.

20 Claims, 5 Drawing Sheets

(56) References Cited

OTHER PUBLICATIONS

Ren, P., et al., Copper-catalyzed cross-coupling of functionalized alkyl halides and tosylates with secondary and tertiary alkyl Grignard reagents, Angew. Chem. Int. Ed., 51, pp. 9110-9113 (Year: 2012).*

Hojeong Yu et al., "Effect of alkyl chain spacer on charge transport in n-type dominant polymer semiconductors with a diketopyrrolopyrrole-thiophene-bithiazole acceptor-donor-acceptor unit", Journal of Materials Chemistry C 2017, 5 (14), pp. 3616-3622.

Iwasaki et al., Copper-catalyzed alkyl-alkyl cross-coupling reactions using hydrocarbon additives: Efficiency of catalyst and roles of additives. Journal of Organic Chemistry 2014, 79 (18), pp. 8522-8532.

Kawabata et al., "Effects of branching position of alkyl side chains on ordering structure and charge transport property in thienothiophenedione- and quinacridone-based semiconducting polymers," Polymer Journal 2017, 49 (1), pp. 169-176.

P Ren et al., "Copper-Catalyzed Cross-Coupling of Functionalized Alkyl Halides and Tosylates with condary and Tertiary Alkyl Grignard ReagentSes, Angew", Chem. Int. Ed., 2012, 51, pp. 9110-9113.

Tamura et al., "Copper-catalyzed coupling of grignard reagents and akyl halides in tetrahydrofuran solutions", Journal of Organometallic Chemistry 1972, 42 (1), pp. 205-228.

Terao et al., "Cross-Coupling Reaction of Alkyl Halides with Grignard Reagents Catalyzed by Ni, Pd, or Cu Complexes with p-Carbon Ligand(s)", Accounts of Chemical Research 2008, 41 (11), pp. 1545-1554.

Van Summeren et al., "Catalytic asymmetric synthesis of enantiopure isoprenoid building blocks: Application in the synthesis of apple leafminer pheromones", Chemical Communications 2005, (11), pp. 1387-1389.

Zeng et al., "Influence of alkyl chain branching point on the electron transport properties of di (perylene diimides) thin film transistors", RSC Advances 2016, 6 (61), pp. 55946-55952.

Zhang et al., "Insight into thin-film stacking modes of p-expanded quinoidal molecules on charge transport property via side-chain engineering", Journal of Materials Chemistry C 2017, 5 (8), 1935-1943.

* cited by examiner

SYNTHESIS OF BRANCHED ALKYL ALCOHOLS BY CU(I)-CATALYZED C-C COUPLING BETWEEN ALKYL GRIGNARD REAGENTS AND ALKYL TOSYLATES

BACKGROUND

This application claims the benefit of priority under 35 U.S.C. § 119 of Chinese Patent Application Serial No. 202010214195.5, filed on Mar. 24, 2020, the content of which is relied upon and incorporated herein by reference in its entirety.

The disclosure relates to synthesis of branched alkyl alcohols by Cu(I)-catalyzed C—C coupling between alkyl Grignard reagents and alkyl tosylates for organo-electronic devices.

SUMMARY

In some embodiments, a method, comprises: providing a mixture including at least one alkyl tosylate and a Grignard reagent; and reacting the at least one alkyl tosylate with the Grignard reagent in a C—C coupling reaction mechanism to form a branched aliphatic alcohol.

In one aspect, which is combinable with any of the other aspects or embodiments, the step of reacting proceeds to a yield of at least 30% completion to form the branched aliphatic alcohol.

In one aspect, which is combinable with any of the other aspects or embodiments, the step of reacting proceeds to a yield of at least 40% completion to form the branched aliphatic alcohol.

In one aspect, which is combinable with any of the other aspects or embodiments, the step of reacting proceeds to a yield of at least 50% completion to form the branched aliphatic alcohol.

In one aspect, which is combinable with any of the other aspects or embodiments, the step of reacting is conducted in the presence of a transition metal-containing catalyst.

In one aspect, which is combinable with any of the other aspects or embodiments, the transition metal-containing catalyst comprises at least one of: $CuCl_2$, CuCl, CuBr, CuI, $CuBr.SMe_2$, or combinations thereof.

In one aspect, which is combinable with any of the other aspects or embodiments, the step of reacting is conducted in a solvent selected from: dimethylacetamide (DMAc), toluene, tetrahydrofuran (THF), dimethylformamide (DMF), benzotrifluoride, hexafluoroisopropanol (HFIP), 1,2-dichloroethane (DCE), dimethoxyethane (DME), hexafluorobenzene, 1,4-dioxane, mesitylene, chlorobenzene, p-xylene, o-dichlorobenzene, 1,2,4-trichlorobenzene, 1-chloronaphthalene, or combinations thereof.

In one aspect, which is combinable with any of the other aspects or embodiments, the mixture further includes at least one of an additive or a ligand.

In one aspect, which is combinable with any of the other aspects or embodiments, the at least one alkyl tosylate is formed by reacting an alcohol with a tosyl-containing compound.

In one aspect, which is combinable with any of the other aspects or embodiments, the step of reacting occurs at a temperature in a range of 0° C. to −100° C.

In one aspect, which is combinable with any of the other aspects or embodiments, the Grignard reagent comprises an alcohol with a protecting group selected from: p-methoxybenzyl alcohol (PMB), tetrahydropyran (THP), or combinations thereof.

In some embodiments, a method, comprises: providing a mixture including at least one alkyl tosylate and a Grignard reagent; and reacting the at least one alkyl tosylate with the Grignard reagent in a C—C coupling reaction mechanism to form a branched aliphatic alcohol, wherein the step of reacting proceeds to a yield of at least 30% completion to form the branched aliphatic alcohol.

In one aspect, which is combinable with any of the other aspects or embodiments, the step of reacting is conducted in the presence of a copper-containing catalyst.

In one aspect, which is combinable with any of the other aspects or embodiments, the copper-containing catalyst comprises at least one of: $CuCl_2$, CuCl, CuI, CuBr, $CuBr.SMe_2$, or combinations thereof.

In one aspect, which is combinable with any of the other aspects or embodiments, the step of reacting occurs at a temperature in a range of 0° C. to −100° C.

In one aspect, which is combinable with any of the other aspects or embodiments, the Grignard reagent comprises an alcohol with a protecting group selected from: p-methoxybenzyl alcohol (PMB), tetrahydropyran (THP), or combinations thereof.

BRIEF DESCRIPTION OF THE DRAWINGS

The disclosure will become more fully understood from the following detailed description, taken in conjunction with the accompanying figures, in which.

DETAILED DESCRIPTION

Figure 1:
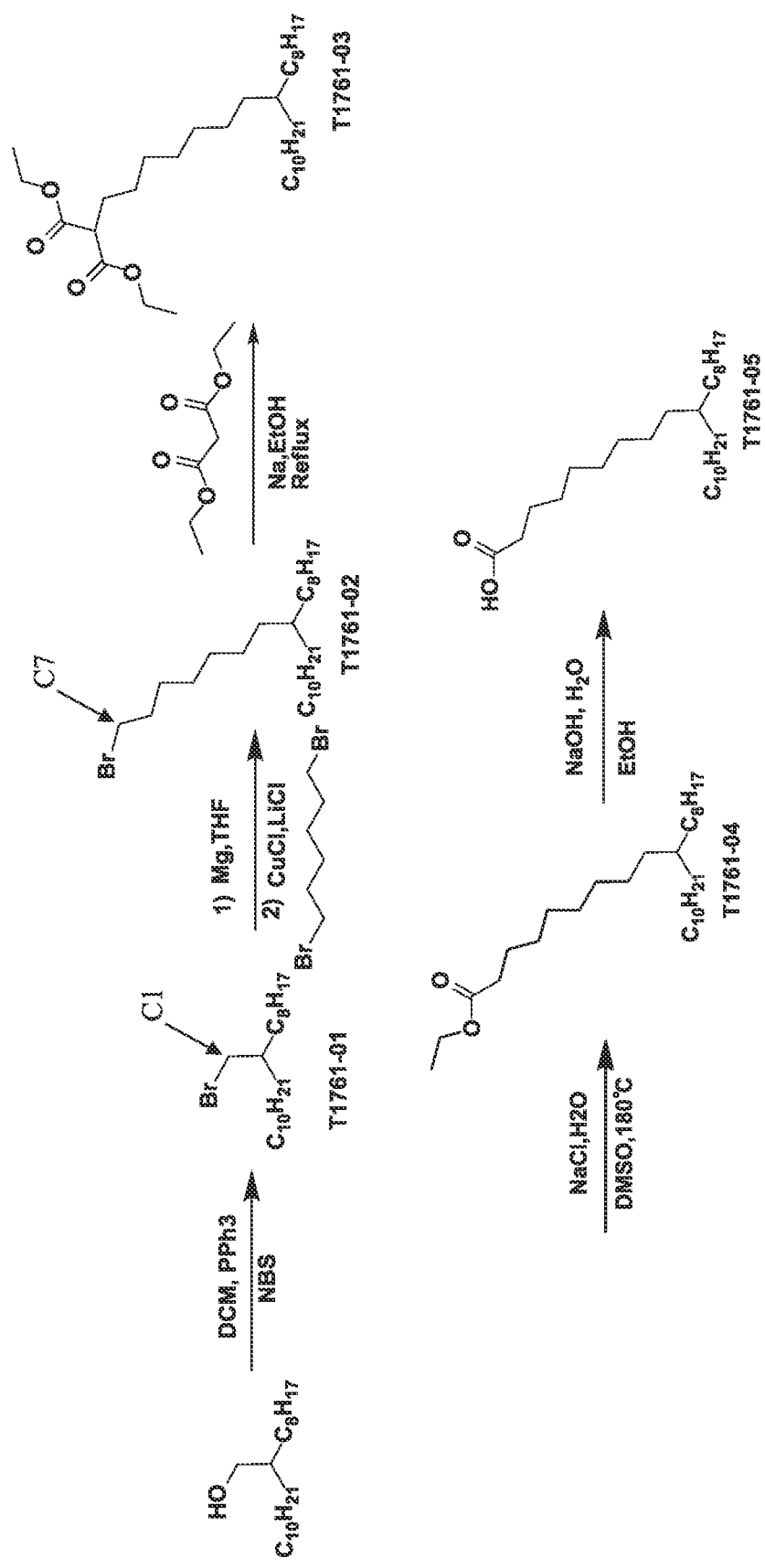
FIG. 1 illustrates a conventional synthesis approach for a branched aliphatic acid.

Reference will now be made in detail to exemplary embodiments which are illustrated in the accompanying drawings. Whenever possible, the same reference numerals will be used throughout the drawings to refer to the same or like parts. The components in the drawings are not necessarily to scale, emphasis instead being placed upon illustrating the principles of the exemplary embodiments. It should be understood that the present application is not limited to the details or methodology set forth in the description or illustrated in the figures. It should also be understood that the terminology is for the purpose of description only and should not be regarded as limiting.

Additionally, any examples set forth in this specification are illustrative, but not limiting, and merely set forth some of the many possible embodiments of the claimed invention. Other suitable modifications and adaptations of the variety of conditions and parameters normally encountered in the field, and which would be apparent to those skilled in the art, are within the spirit and scope of the disclosure.

Definitions

The term "alkyl group" refers to a monoradical branched or unbranched saturated hydrocarbon chain having 1 to 40 carbon atoms. This term is exemplified by groups such as methyl, ethyl, n-propyl, isopropyl, n-butyl, isobutyl, t-butyl, pentyl, n-hexyl, n-heptyl, n-octyl, n-decyl, or tetradecyl, and the like. The alkyl group can be substituted or unsubstituted.

The term "substituted alkyl group" refers to: (1) an alkyl group as defined above, having 1, 2, 3, 4 or 5 substituents, typically 1 to 3 substituents, selected from the group consisting of alkenyl, alkynyl, alkoxy, aralkyl, aldehyde, cycloalkyl, cycloalkenyl, acyl, acylamino, acyl halide, acyloxy, amino, aminocarbonyl, alkoxycarbonylamino, azido, cyano, halogen, hydroxy, keto, thiocarbonyl, carboxy, carboxyalkyl, arylthiol, ester, heteroarylthio, heterocyclylthio, hydroxyl, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl and —SO$_2$-heteroaryl, thioalkyl, vinyl ether. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2; or (2) an alkyl group as defined above that is interrupted by 1-10 atoms independently chosen from oxygen, sulfur and NR$_a$, where R$_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF$_3$, amino, substituted amino, cyano, or —S(O)$_n$R$_{SO}$, in which R$_{SO}$ is alkyl, aryl, or heteroaryl and n is 0, 1 or 2; or (3) an alkyl group as defined above that has both 1, 2, 3, 4 or 5 substituents as defined above and is also interrupted by 1-10 atoms as defined above. For example, the alkyl groups can be an alkyl hydroxy group, where any of the hydrogen atoms of the alkyl group are substituted with a hydroxyl group.

The term "alkyl group" as defined herein also includes cycloalkyl groups. The term "cycloalkyl group" as used herein is a non-aromatic carbon-based ring (i.e., carbocyclic) composed of at least three carbon atoms, and in some embodiments from three to 20 carbon atoms, having a single cyclic ring or multiple condensed rings. Examples of single ring cycloalkyl groups include, but are not limited to, cyclopropyl, cyclobutyl, cyclopentyl, cyclohexyl, cyclooctyl, and the like. Examples of multiple ring cycloalkyl groups include, but are not limited to, adamantanyl, bicyclo[2.2.1]heptane, 1,3,3-trimethylbicyclo[2.2.1]hept-2-yl, (2,3,3-trimethylbicyclo[2.2.1]hept-2-yl), or carbocyclic groups to which is fused an aryl group, for example indane, and the like. The term cycloalkyl group also includes a heterocycloalkyl group, where at least one of the carbon atoms of the ring is substituted with a heteroatom such as, but not limited to, nitrogen, oxygen, sulfur, or phosphorus.

The term "unsubstituted alkyl group" is defined herein as an alkyl group composed of just carbon and hydrogen.

The term "acyl" denotes a group —C(O)R$_{CO}$, in which R$_{CO}$ is hydrogen, optionally substituted alkyl, optionally substituted cycloalkyl, optionally substituted heterocyclyl, optionally substituted aryl, and optionally substituted heteroaryl.

The term "aryl group" as used herein is any carbon-based aromatic group (i.e., aromatic carbocyclic) such as having a single ring (e.g., phenyl) or multiple rings (e.g., biphenyl), or multiple condensed (fused) rings (e.g., naphthyl or anthryl). These may include, but are not limited to, benzene, naphthalene, phenyl, etc.

The term "aryl group" also includes "heteroaryl group," meaning a radical derived from an aromatic cyclic group (i.e., fully unsaturated) having 1, 2, 3, 4, 5, 6, 7, 8, 9, 10, 11, 12, 13, 14, or 15 carbon atoms and 1, 2, 3 or 4 heteroatoms selected from oxygen, nitrogen, sulfur, and phosphorus within at least one ring. In other words, heteroaryl groups are aromatic rings composed of at least three carbon atoms that has at least one heteroatom incorporated within the ring of the aromatic group. Such heteroaryl groups can have a single ring (e.g., pyridyl or furyl) or multiple condensed rings (e.g., indolizinyl, benzothiazolyl, or benzothienyl). Examples of heteroaryls include, but are not limited to, [1,2,4]oxadiazole, [1,3,4]oxadiazole, [1,2,4]thiadiazole, [1,3,4]thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, triazole, oxazole, thiazole, naphthyridine, and the like as well as N-oxide and N-alkoxy derivatives of nitrogen containing heteroaryl compounds, for example pyridine-N-oxide derivatives.

Unless otherwise constrained by the definition for the heteroaryl substituent, such heteroaryl groups can be optionally substituted with 1 to 5 substituents, typically 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The aryl group can be substituted or unsubstituted. Unless otherwise constrained by the definition for the aryl substituent, such aryl groups can optionally be substituted with from 1 to 5 substituents, typically 1 to 3 substituents, selected from the group consisting of alkyl, alkenyl, alkynyl, alkoxy, aldehyde, cycloalkyl, cycloalkenyl, acyl, acylamino, acyloxy, amino, aminocarbonyl, alkoxycarbonylamino, azido, cyano, ester, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2. In some embodiments, the term "aryl group" is limited to substituted or unsubstituted aryl and heteroaryl rings having from three to 30 carbon atoms.

The term "aralkyl group" as used herein is an aryl group having an alkyl group or an alkylene group as defined herein covalently attached to the aryl group. An example of an aralkyl group is a benzyl group. "Optionally substituted aralkyl" refers to an optionally substituted aryl group covalently linked to an optionally substituted alkyl group or alkylene group. Such aralkyl groups are exemplified by benzyl, phenylethyl, 3-(4-methoxyphenyl)propyl, and the like.

The term "heteroaralkyl" refers to a heteroaryl group covalently linked to an alkylene group, where heteroaryl and alkylene are defined herein. "Optionally substituted heteroaralkyl" refers to an optionally substituted heteroaryl group covalently linked to an optionally substituted alkylene group. Such heteroaralkyl groups are exemplified by 3-pyridylmethyl, quinolin-8-ylethyl, 4-methoxythiazol-2-ylpropyl, and the like.

The term "alkenyl group" refers to a monoradical of a branched or unbranched unsaturated hydrocarbon group typically having from 2 to 40 carbon atoms, more typically 2 to 10 carbon atoms and even more typically 2 to 6 carbon atoms and having 1-6, typically 1, double bond (vinyl). Typical alkenyl groups include ethenyl or vinyl ($—CH═CH_2$), 1-propylene or allyl ($—CH_2CH═CH_2$), isopropylene ($—C(CH_3)═CH_2$), bicyclo[2.2.1]heptene, and the like. When alkenyl is attached to nitrogen, the double bond cannot be alpha to the nitrogen.

The term "substituted alkenyl group" refers to an alkenyl group as defined above having 1, 2, 3, 4 or 5 substituents, and typically 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR_{SO}$, where $R_{SO}$ is alkyl, aryl, or heteroaryl and n is 0, 1 or 2.

The term "cycloalkenyl group" refers to carbocyclic groups of from 3 to 20 carbon atoms having a single cyclic ring or multiple condensed rings with at least one double bond in the ring structure.

The term "alkynyl group" refers to a monoradical of an unsaturated hydrocarbon, typically having from 2 to 40 carbon atoms, more typically 2 to 10 carbon atoms and even more typically 2 to 6 carbon atoms and having at least 1 and typically from 1-6 sites of acetylene (triple bond) unsaturation. Typical alkynyl groups include ethynyl, ($—C≡CH$), propargyl (or prop-1-yn-3-yl, $—CH_2C≡CH$), and the like. When alkynyl is attached to nitrogen, the triple bond cannot be alpha to the nitrogen.

The term "substituted alkynyl group" refers to an alkynyl group as defined above having 1, 2, 3, 4 or 5 substituents, and typically 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR_{SO}$, where $R_{SO}$ is alkyl, aryl, or heteroaryl and n is 0, 1 or 2.

The term "alkylene group" is defined as a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, typically 1-10 carbon atoms, more typically 1, 2, 3, 4, 5 or 6 carbon atoms. This term is exemplified by groups such as methylene ($—CH_2—$), ethylene ($—CH_2CH_2—$), the propylene isomers (e.g., $—CH_2CH_2CH_2—$ and $—CH(CH_3)CH_2—$) and the like.

The term "substituted alkylene group" refers to: (1) an alkylene group as defined above having 1, 2, 3, 4, or 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, —$SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR_{SO}$, where $R_{SO}$ is alkyl, aryl, or heteroaryl and n is 0, 1 or 2; or (2) an alkylene group as defined above that is interrupted by 1-20 atoms independently chosen from oxygen, sulfur and $NR_a—$, where $R_a$ is chosen from hydrogen, optionally substituted alkyl, cycloalkyl, cycloalkenyl, aryl, heteroaryl and heterocyclyl, or groups selected from carbonyl, carboxyester, carboxyamide and sulfonyl; or (3) an alkylene group as defined above that has both 1, 2, 3, 4 or 5 substituents as defined above and is also interrupted by 1-20 atoms as defined above. Examples of substituted alkylenes are chloromethylene ($—CH(Cl)—$), aminoethylene ($—CH(NH_2)CH_2—$), methylaminoethylene ($—CH(NHMe)CH_2—$), 2-carboxypropylene isomers ($—CH_2CH(CO_2H)CH_2—$), ethoxyethyl ($—CH_2CH_2O—CH_2CH_2—$), ethylmethylaminoethyl ($—CH_2CH_2N(CH_3)CH_2CH_2—$), and the like.

The term "alkoxy group" refers to the group R—O—, where R is an optionally substituted alkyl or optionally substituted cycloalkyl, or R is a group —Y—Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Typical alkoxy groups are optionally substituted alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "alkylthio group" refers to the group $R_S$—S—, where $R_S$ is as defined for alkoxy.

The term "aminocarbonyl" refers to the group —C(O)$NR_NR_N$ where each $R_N$ is independently hydrogen, alkyl, aryl, heteroaryl, heterocyclyl or where both $R_N$ groups are joined to form a heterocyclic group (e.g., morpholino). Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —$S(O)_nR_{SO}$, where $R_{SO}$ is alkyl, aryl, or heteroaryl and n is 0, 1 or 2.

The term "acylamino" refers to the group —NR$_{NCO}$C(O)R where each R$_{NCO}$ is independently hydrogen, alkyl, aryl, heteroaryl, or heterocyclyl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may be optionally further substituted by alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "aryloxy group" refers to the group aryl-O— wherein the aryl group is as defined above, and includes optionally substituted aryl groups as also defined above.

The term "heteroaryloxy" refers to the group heteroaryl-O—.

The term "amino" refers to the group —NH$_2$.

The term "substituted amino" refers to the group —NR$_w$R$_w$ where each R$_w$ is independently selected from the group consisting of hydrogen, alkyl, cycloalkyl, carboxyalkyl (for example, benzyloxycarbonyl), aryl, heteroaryl and heterocyclyl provided that both R$_w$ groups are not hydrogen, or a group —Y—Z, in which Y is optionally substituted alkylene and Z is alkenyl, cycloalkenyl, or alkynyl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "carboxy" refers to a group —C(O)OH. The term "carboxyalkyl group" refers to the groups —C(O)O-alkyl or —C(O)O-cycloalkyl, where alkyl and cycloalkyl, are as defined herein, and may be optionally further substituted by alkyl, alkenyl, alkynyl, alkoxy, halogen, CF$_3$, amino, substituted amino, cyano, and —S(O)$_n$R$_{SO}$, in which R$_{SO}$ is alkyl, aryl, or heteroaryl and n is 0, 1 or 2.

The terms "substituted cycloalkyl group" or "substituted cycloalkenyl group" refer to cycloalkyl or cycloalkenyl groups having 1, 2, 3, 4 or 5 substituents, and typically 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "conjugated group" is defined as a linear, branched or cyclic group, or combination thereof, in which p-orbitals of the atoms within the group are connected via delocalization of electrons and wherein the structure can be described as containing alternating single and double or triple bonds and may further contain lone pairs, radicals, or carbenium ions. Conjugated cyclic groups may comprise both aromatic and non-aromatic groups, and may comprise polycyclic or heterocyclic groups, such as diketopyrrolopyrrole. Ideally, conjugated groups are bound in such a way as to continue the conjugation between the thiophene moieties they connect. In some embodiments, "conjugated groups" is limited to conjugated groups having three to 30 carbon atoms.

The term "halogen," "halo," or "halide" may be referred to interchangeably and refer to fluoro, bromo, chloro, and iodo.

The term "heterocyclyl" refers to a monoradical saturated or partially unsaturated group having a single ring or multiple condensed rings, having from 1 to 40 carbon atoms and from 1 to 10 hetero atoms, typically 1, 2, 3 or 4 heteroatoms, selected from nitrogen, sulfur, phosphorus, and/or oxygen within the ring. Heterocyclic groups can have a single ring or multiple condensed rings, and include tetrahydrofuranyl, morpholino, piperidinyl, piperazino, dihydropyridino, and the like.

Unless otherwise constrained by the definition for the heterocyclyl substituent, such heterocyclyl groups can be optionally substituted with 1, 2, 3, 4 or 5, and typically 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "thiol" refers to the group —SH. The term "substituted alkylthio" refers to the group —S-substituted alkyl. The term "arylthiol group" refers to the group aryl-S—, where aryl is as defined as above. The term "heteroarylthiol" refers to the group —S-heteroaryl wherein the heteroaryl group is as defined above including optionally substituted heteroaryl groups as also defined above.

The term "sulfoxide" refers to a group —S(O)R$_{SO}$, in which R$_{SO}$ is alkyl, aryl, or heteroaryl. The term "substituted sulfoxide" refers to a group —S(O)R$_{SO}$, in which R$_{SO}$ is substituted alkyl, substituted aryl, or substituted heteroaryl, as defined herein. The term "sulfone" refers to a group —S(O)$_2$R$_{SO}$, in which R$_{SO}$ is alkyl, aryl, or heteroaryl. The term "substituted sulfone" refers to a group —S(O)$_2$R$_{SO}$, in which R$_{SO}$ is substituted alkyl, substituted aryl, or substituted heteroaryl, as defined herein.

The term "keto" refers to a group —C(O)—. The term "thiocarbonyl" refers to a group —C(S)—.

As used herein, the term "room temperature" is 20° C. to 25° C.

Disclosed are compounds, compositions, and components that can be used for, can be used in conjunction with, can be used in preparation of, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C—F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A weight percent of a component, unless specifically stated to the contrary, is based on the total weight of the formulation or composition in which the component is included.

Compared to small molecules, one advantage of using organic semiconducting (OSC) polymers in organo-electronic devices (e.g., organic thin-film transistor (OTFT) arrays, organic field-effect transistors (OFETs), organic light-emitting diode (OLED) panels, organic photovoltaic (OPV) solar panels, pressure sensors, etc.) is that they are solution processable. For example, solution-based processes (e.g., spin-coating, slot-die coating, inkjet printing, etc.) are currently used in mass-production of large-area organo-electronic devices. Successful application of low-temperature, solution-based processes may significantly reduce production costs of organo-electronic devices.

However, a trade-off exists between intrinsic electronic performance of OSC polymers and their processability: higher molecular weight OSC polymers have better electronic performance (e.g., higher charge mobility); too high molecular weight OSC polymers have poor solubilities in commonly used organic solvents. As a result, solution-based processing is difficult implement in current systems, thereby offsetting the advantage in using OSC polymers for industrial applications.

One way to address this issue is by side-chain engineering, or in other words, optimizing solubility of polymers in desired solvents by manipulation of polymer side chains. For example, solubility of poly(3-hexylthiophene) (P3HT) is significantly higher than its non-side chain polythiophene counterpart. In other words, solubilities of OSC polymers in organic solution improve by introducing alkyl side chains, which include both linear side chains and branched side chains. For linear alkyl side chains, it is difficult to manufacture chain lengths longer than 18 due to raw material constraints. Conversely, branched side chains are more efficient in terms of solubility improvement because compared with linear side chains, they provide a higher density of alkyl carbon atoms. For branched side chains, commonly used raw materials include 2-octyldodecanol, which occurs as a natural product and can also be synthesized by condensation of two n-decanols, and 1-tetradecanol.

Moreover, the branching position of alkyl side chains may have an effect on ordering structure and charge transport property in OSC small molecules and polymers. Whether a far away branching position (at least four (4) carbons away from the aromatic structure) is beneficial for OSC molecular ordering and electronic performance depends on at least molecular structures, as well as other factors, such as ease of formation of π-π stacking structures. For most OSC polymers (both p-type and n-type), moving the branching position far away from the OSC polymer backbone reduces π-π stacking d-spacing distances, thereby significantly improving the polymers' electronic performance.

The present disclosure describes a low-cost, high-atom efficient method to synthesize branched alkyl alcohols, which are used as key raw materials for side chains of OSC polymers, by Cu(I)-catalyzed (e.g., $CuBr.SMe_2$-catalyzed) C—C cross-coupling between alkyl Grignard reagents and alkyl tosylates. In some embodiments, Cu-, Ni-, and Pd-based catalysts are also contemplated for the C—C cross-coupling reaction. No other ligands or additives are necessary. Results indicate that $CuBr.SMe_2$ is an efficient catalyst, as compared with other commonly used Cu/ligand/additive systems. The disclosed synthesis of branched alkyl alcohols significantly reduces the cost of branched side-chain grafted OSC polymers.

EXAMPLES

The embodiments described herein will be further clarified by the following examples.

Comparative Example 1

FIG. 1 illustrates a conventional synthesis approach for a branched aliphatic acid, designated as T1761-05. In one key step, T1761-01 is transformed to T1761-02, whereby the branching point is altered from C1 to C7 by a CuCl-catalyzed C—C coupling of Grignard reagent of T1761-01 and 1,6-dibromohexane. T1761-02 is then transformed into the target compound T1761-05 via three additional steps. In this manner, though the synthesis of T1761-05 is scalable, complex processing steps are needed, and atom efficiency is low. Atom efficiency (i.e., atom economy) is the conversion efficiency of a chemical process in terms of all atoms involved and the desired products produced and can be defined as: [molecular weight of desired product, $M_w(P)$)/(molecular weight of all reactants, $M_w(R_{TOT})$)]×100%. For a multi-step process, where intermediates are formed in one step and consumed during a later step (e.g., A+B→C; C+D→E; and E+F→G), atom efficiency may equal: $M_w(G)/M_w(A+B+C+D+E+F)$. Atom economy is different from chemical yield, because a high-yielding process may still result in substantial byproducts. As a result of low atom efficiency, the overall cost of synthesizing T1761-05 is high. Therefore, in order to provide low-cost OSC polymers, the present disclosure presents a more cost-efficient approach in synthesizing branched aliphatic acids (e.g., T1761-05), which may be utilized in optimizing solubility electronic performance of the OSC polymers for organo-electronic applications.

Example 2—Overall Reaction Scheme

Figure 2:
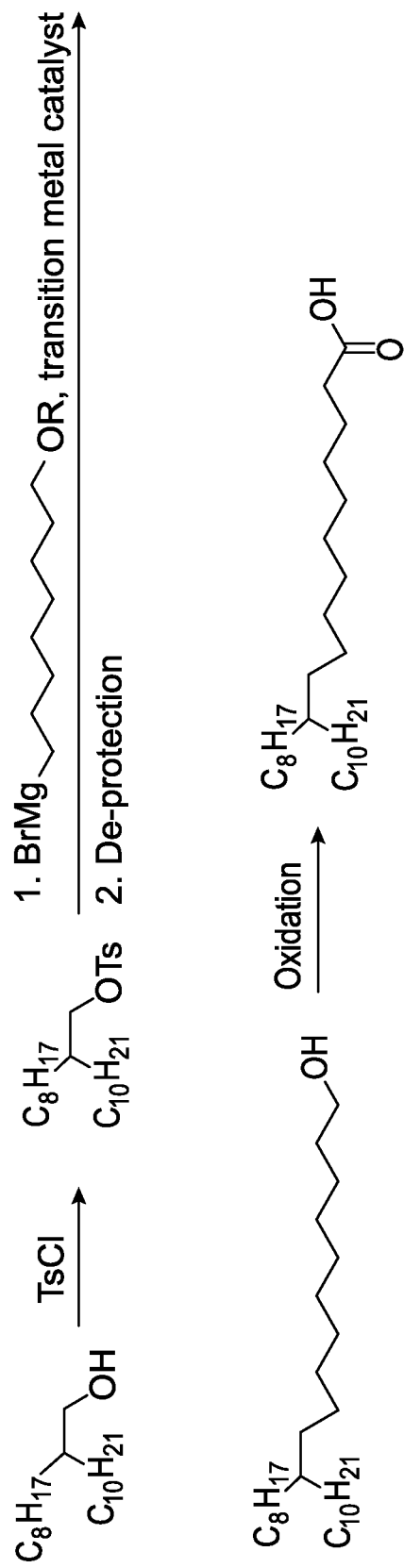
FIG. 2 illustrates a general synthesis approach for a branched aliphatic acid, according to some embodiments.

Described herein are two possible ways of reducing the cost of T1761-05 synthesis: moving the branching position from C1 to C9 with only one C—C coupling reaction and/or making the key C—C coupling reaction more efficient. In one key step, the branching position is altered from C1 to C9 by a transition metal-catalyzed C—C coupling reaction with an alkyl Grignard reagent (comprising a protected alcohol) and an alkyl tosylate as starting materials (FIG. 2). The transition metal catalyst of FIG. 2 may include Pd-, Ni-, and/or Cu-based transition metal complexes. This new synthetic strategy for T1761-05 has a higher atom efficiency and lower synthesis cost than comparative Example 1.

Example 3—Selection of Catalyst

Selection of the catalyst for C—C coupling of alkyl tosylate and Grignard reagent was optimized based on Reaction 1 (shown below). Tested catalysts are shown in Table 1 below.

Copper-based catalysts, which are widely used for C—C coupling involving Grignard reagents, are cheaper and more environmentally benign than nickel-based, palladium-based, and certain Li-containing (e.g., $Li_2CuCl_4$) catalysts.

Reaction 1

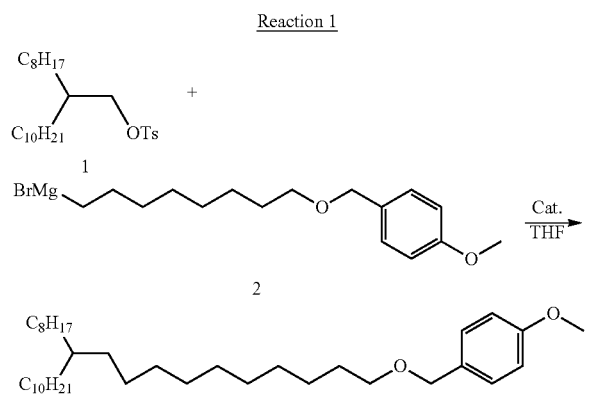

TABLE 1

| Entry | Catalyst | Additives | Ligand | Yield |
| --- | --- | --- | --- | --- |
| 1[a] | $CuCl_2$ | | | 0 |
| 2[a] | $CuCl_2$ | | NMP | 0 |
| 3[a] | $CuCl_2$ | LiCl | NMP | 0 |
| 4[a] | $CuCl_2$ | | Ph—≡—$CH_3$ | 39 |
| 5[a] | CuI | LiOMe | TMEDA | 44 |
| 6[a] | CuBr·$SMe_2$ | | | 0 |
| 7[b] | CuBr·$SMe_2$ | | | 54 |

[a]Conditions: Concetration of 1 and 2 from Reaction 1 was 3 mmol and 4.5 mmol, respectively; catalyst (10 mol. %), THF (10 mL), additives (1 equiv.), ligand (20 mol. %), at 0° C.
[b]Conditions for entry 7 is same as entries 1-6, except that reaction was carried out at −78° C.

Entries 1-4 are for $CuCl_2$ evaluated under different reaction conditions. None of entries 1-3 were able to yield any product in Reaction 1, and only with a phenylmethylacetylene π-carbon ligand was a moderate yield obtained at 39%. In other words, phenylmethylacetylene (entry 4), which is a π-carbon ligand, is necessary for $CuCl_2$ to exhibit catalytic activity. And while CuI with LiOMe afforded a yet higher yield at 44% with tetramethyl ethylenediamine (TMEDA) as a (entry 5), in general, catalysis systems using ligands and additives are complex and costly.

In general, for homogeneous catalysis, the inclusion of organic ligands in a catalytic reactions serve two functions: (1) coordination of organic ligands improves solubility of metal-based catalysts, thereby allowing catalyst dissolution in solvents and catalyzed chemical reactions; and (2) coordinated ligands modify electronic and steric environments of catalyst metal centers, such that catalysts of desired reactivity and selectivity can be obtained. Additives mostly do not coordinate with the catalyst, but rather, functions as an oxidant/reductant or neutralizer, the latter which reacts with bases/acids generated from catalytic reactions. However, both ligands and additives are either very expensive, not commercially available, or are toxic for the environment. For the reactions disclosed herein, neither ligands nor additives are necessary components for the mechanism.

$CuBr.SMe_2$ was tested at two different reaction conditions. Entry 6 was conducted at 0° C. and entry 7 was conducted at −78° C. Yield increased significantly from 0% to 54% with the lowered reaction temperature. Thermodynamics is a key consideration underlying the mechanisms disclosed herein. In practice, temperatures have a significant impact on almost all chemical and biological transformations, with the general trend being that higher temperatures lead to higher reactivities and faster transformations, but also lower selectivity and stability. In the instant case, higher yield at lower temperature results in higher selectivity toward the desired product. At 0° C., chemical reactions are taking place, but none of them lead to the desired product.

Example 4—Effect of Protecting Group ('R' Group) of Grignard Reagent on Yield

Two different 'R' groups on the Grignard reagent were tested to determine the effects protecting groups have on yield in C—C coupling reactions. Reaction 2, which is analogous to Entry 4 of Table 1 above, is shown below and described the influence of protecting groups p-methoxybenzyl alcohol (PMB) (39% yield) and tetrahydropyran (THP) (0% yield).

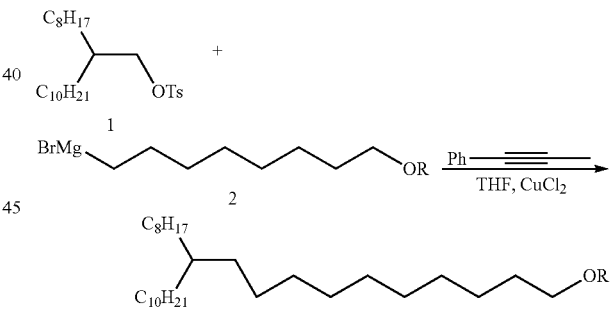

Conditions: Concentrations of 1 and 2 from Reaction 2 were 3 mmol and 4.5 mmol, respectively; $CuCl_2$ catalyst (10 mol. %), THE (10 mL) at 0° C.

Reaction 2

In some embodiments, other protecting groups may be contemplated such as: esters, ethers, and silyl ethers, which are mainly used as protecting groups for alcohols. Commonly used reagents to form esters include, but are not limited to: isopropenyl acetate, acetic anhydride, and various acids, such as $CF_3COOH$, HCOOH, $H_2C$=CHCOOH, EtCOOH and PrCOOH. Commonly used reagents to form ethers include, but are not limited to: enol esters, p-methoxybenzyl alcohol (PMB), benzyl alcohol, p-chlorobenzyl alcohol and tetrahydropyran (THP). Commonly used reagents to form silyl ethers include, but are not limited to: tert-butyldiphenylsilyl (TBDPS), tert-butyldimethylsilyl (TBS) and triethylsilyl (TES).

Example 5—Synthesis of 11-octylhenicosan-1-ol

Step 1: Synthesis of TM1-1
TM1-1 was formed according to Reaction 3 below.

Reaction 3

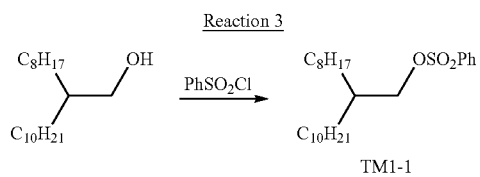

TM1-1

TsCl (7.92 g, 40 mmol) in dichloromethane (DCM) (20 mL) was added dropwise to 2-octyl-1-dodecanol (CAS No. 5333-42-6) (6 g, 20 mmol), triethylamine (Et$_3$N) (6 g, 60 mmol) and 4-dimethylaminopyridine (DMAP) (2.4 g, 20 mmol) in DCM (20 mL) at 0° C. under N$_2$. The mixture was stirred at room temperature (20° C. to 25° C.) for 18 hrs. and then purified by chromatography on silica gel (PE:EA=100:1) to get a colorless oil with 95%-98% yield.

Step 2: Synthesis of TM1-2
TM1-2 was formed according to Reaction 4 below.

Reaction 4

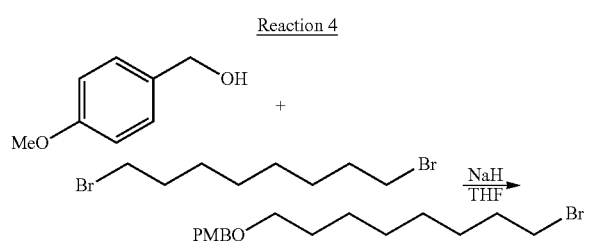

Figure 3:
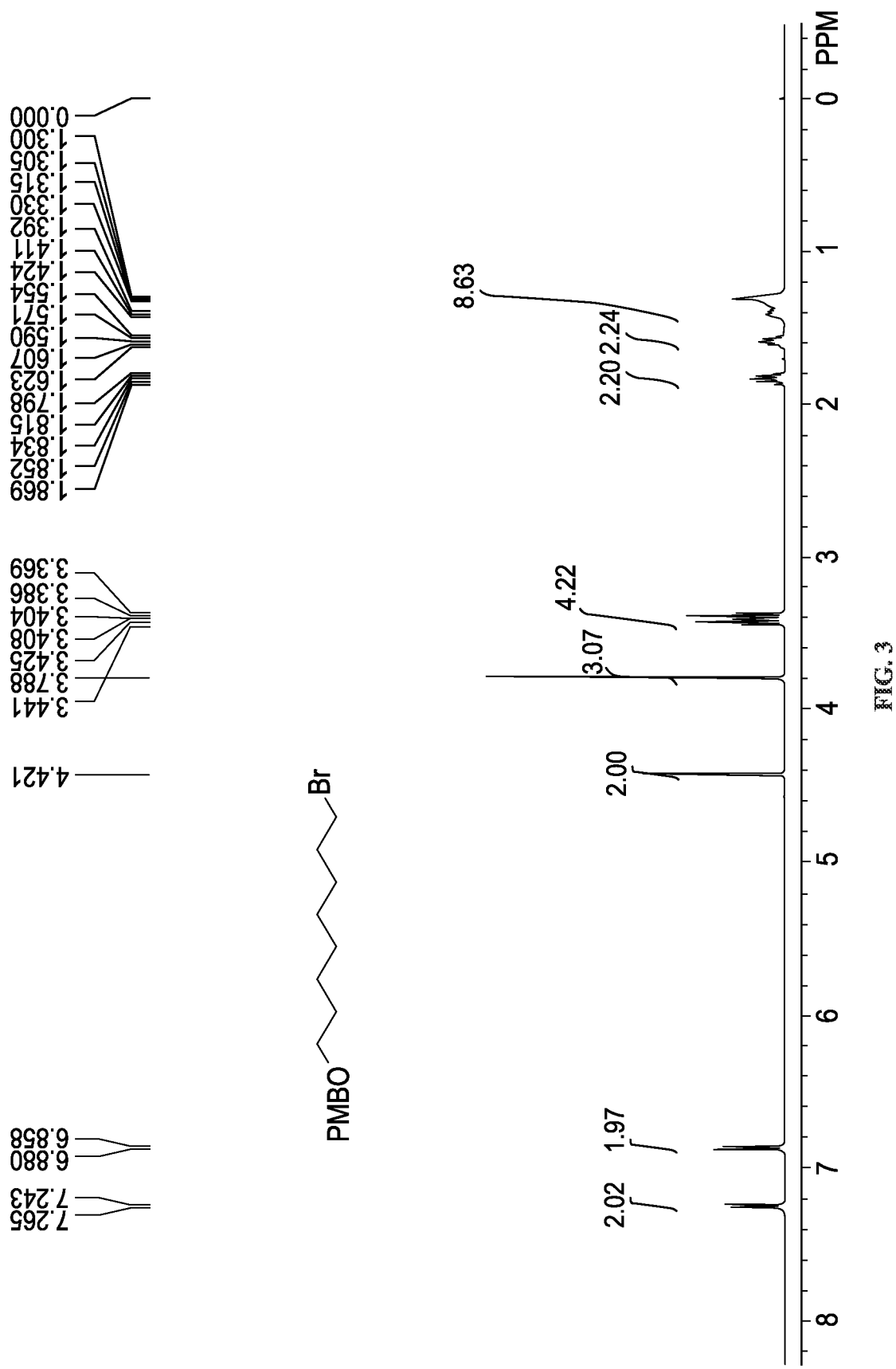
FIG. 3 illustrates $^1H$ NMR spectra of TM1-2, according to some embodiments.

To a suspension of sodium hydride (60% in oil, 2.2 g, 55 mmol) in tetrahydrofuran (THF) (100 mL) at 0° C., p-methoxybenzyl alcohol (PMB) (6.9 g, 50 mmol) was added. The mixture was stirred at 0° C. for 1 hr. and 1,8-dibromooctane was added (18.5 mL, 100 mmol) thereafter. After warming to room temperature and stirring for about 20 hrs., the reaction was quenched with saturated ammonium chloride (NH$_4$Cl) and extracted with ethyl acetate (EtOAc) (20 mL×3 times). The combined organic solutions were dried over MgSO$_4$, filtered, and concentrated under reduced pressure. The crude product was purified by chromatography on silica gel (gradient PE/EtOAc 10/0 to 9/1) to afford PMB-protected compound (7.1 g, 43%) as pale yellow oil. FIG. 3 illustrates $^1$H NMR spectra of TM1-2 with characteristics peaks at 7.26 (d, J=8.8 Hz, 2H), 6.87 (d, J=8.8 Hz, 2H), 4.42 (s, 2H), 3.79 (s, 3H), 3.45-3.35 (m, 4H), 1.87-1.78 (m, 2H), 1.64-1.54 (m, 2H), 1.44-1.30 (m, 8H).

Step 3: Synthesis of TM1-3
TM1-3 was formed according to Reaction 5 below.

Reaction 5

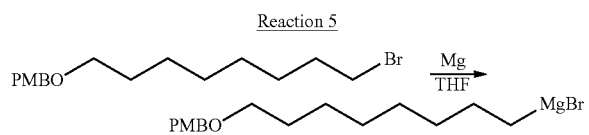

TM1-3

The PMB-protected compound (30 mmol) in dry THE (30 mL) was added dropwise to Mg (1.094 g, 45 mmol, 1.5 eq) and THE (30 mL) in an argon-purged flask and then stirred for 1.5 to 2 hrs. at room temperature. The resulting solution was immediately consumed. The Grignard reagent (30 mmol, 2.0 eq) was added in a dropwise fashion to a solution of TM1-1 (6.79 g, 15 mmol) and CuBr.SMe$_2$ (0.65 g, 3.15 mmol, 21 mol %) in dry THE (15 mL) at −78° C. under argon. After stirring for 1 hour at −78° C., the solution was slowly warmed to room temperature and stirred overnight. The reaction was quenched with saturated NH$_4$Cl, extracted with Et$_2$O (20 mL×3 times) and the combined organic layers were washed with brine, dried over MgSO$_4$ and concentrated. The crude product was purified by chromatography on silica gel (PE:EA=500:1) to get a pale yellow oil (5.2 g, 65%).

Figure 4:
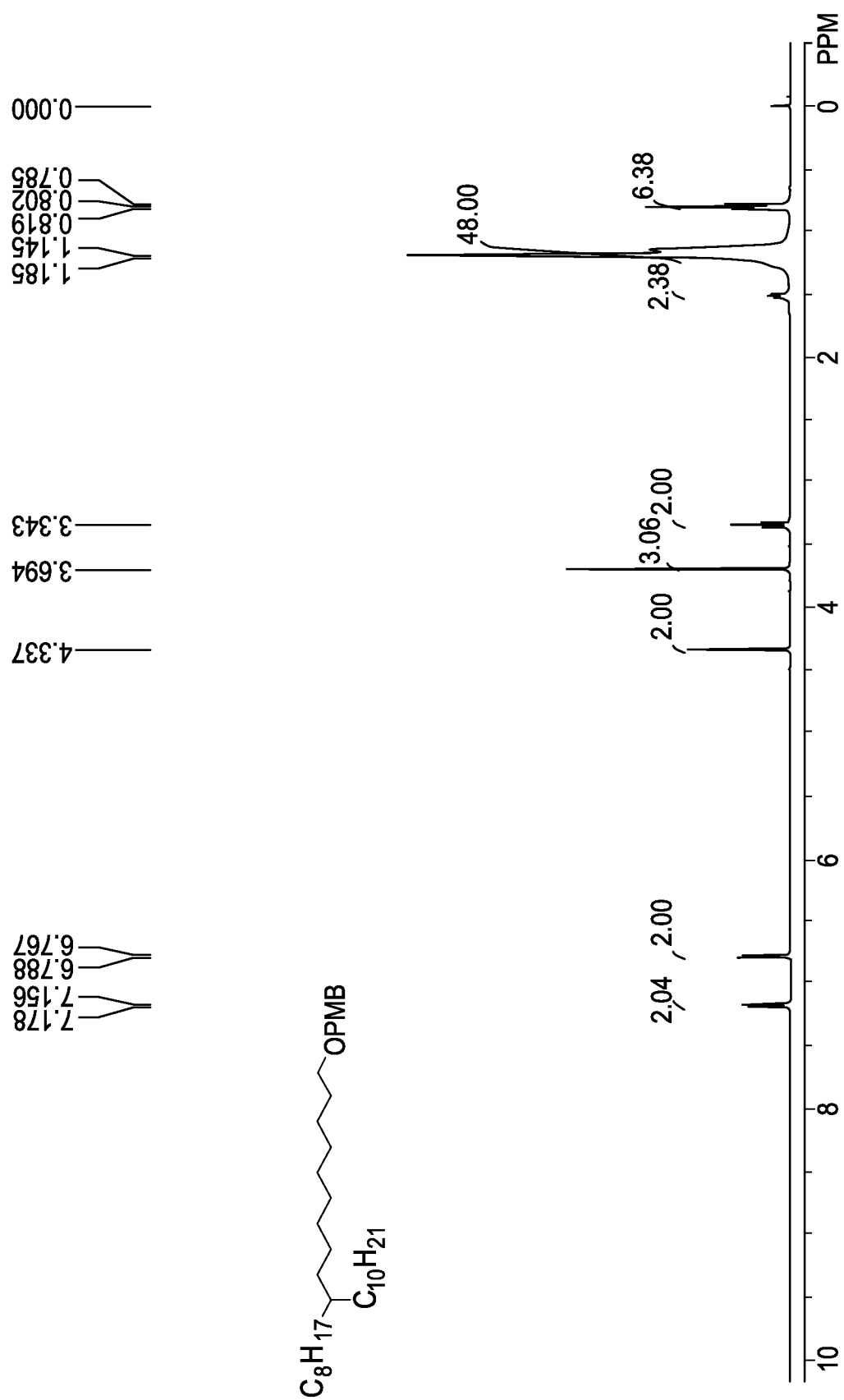
FIG. 4 illustrates $^1H$ NMR spectra of TM1-3, according to some embodiments.
Figure 5:
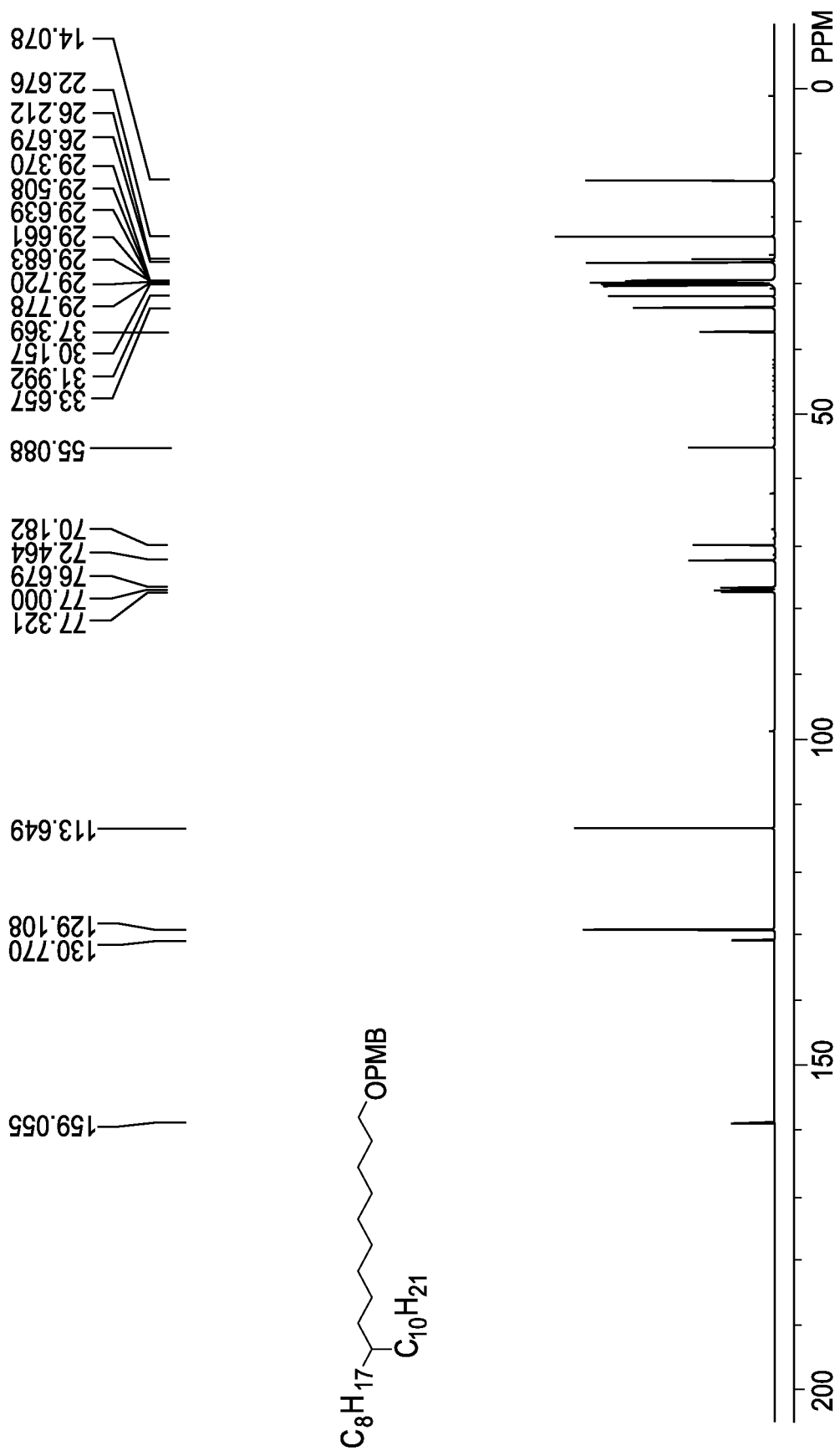
FIG. 5 illustrates $^{13}C$ NMR spectra of TM1-3, according to some embodiments.

FIG. 4 illustrates $^1$H NMR spectra of TM1-3 with characteristics peaks at 7.17 (d, J=8.8 Hz, 2H), 6.78 (d, J=8.8 Hz, 2H), 4.34 (s, 2H), 3.69 (s, 3H), 3.38-3.31 (m, 2H), 1.56-1.48 (m, 2H), 1.18-1.13 (m, 47H), 0.80 (t, J=6.8 Hz, 6H. FIG. 5 illustrates $^{13}$C NMR spectra of TM1-3 with characteristics peaks at 159.06, 130.77, 129.11, 113.65, 72.46, 70.18, 55.09, 37.37, 33.67, 31.92, 30.15, 29.78, 29.72, 29.68, 29.66, 29.64, 29.51, 29.37, 26.68, 26.21, 22.68, 14.08.

Step 4: Synthesis of 11-octylhenicosan-1-ol
11-octylhenicosan-1-ol was formed according to Reaction 6 below.

Reaction 6

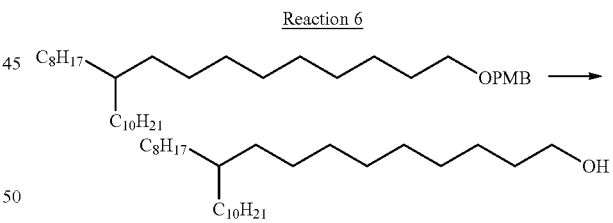

Boron trichloride (2 equiv. 1 M in CH$_2$Cl$_2$) was added to a 0.05M solution of the PMB-protected alcohol from Reaction 5 (10 mmol, 5.3 g, 1 equiv.) in CH$_2$Cl$_2$ at −78° C. The reaction mixture was warmed to room temperature, stirred for 2 hrs., quenched with MeOH, and diluted with water. The organic layer was washed with water, dried over MgSO$_4$, filtrated and concentrated under reduced pressure. The crude product was purified by chromatography on silica gel (3.3 g, 80%).

Characterization Techniques
Proton nuclear magnetic resonance ($^1$H-NMR) was measured with a Bruker 400 MHz spectrometer in CDCl$_3$ (FIGS. 3, 4). Carbon-13 nuclear magnetic resonance ($^{13}$C-NMR) was measured with a Bruker 100 MHz spectrometer in CDCl$_3$ (FIG. 5).

As provided herein, successful synthesis of branched alkyl alcohols by Cu(I)-catalyzed C—C coupling between alkyl Grignard reagents and alkyl tosylates are demonstrated. Branched alkyl alcohols may be useful as key raw materials for side chains of OSC polymers for organo-electronic devices. Advantages include: (1) significant reduction in the cost of branched alkyl alcohols, as well as branched side-chain grafted OSC polymers; (2) easier side-chain engineering for OSC polymers; and (3) reliable scale-up for industrial applications.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

As utilized herein, "optional," "optionally," or the like are intended to mean that the subsequently described event or circumstance can or cannot occur, and that the description includes instances where the event or circumstance occurs and instances where it does not occur. The indefinite article "a" or "an" and its corresponding definite article "the" as used herein means at least one, or one or more, unless specified otherwise.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

It will be apparent to those skilled in the art that various modifications and variations can be made without departing from the spirit or scope of the claimed subject matter. Accordingly, the claimed subject matter is not to be restricted except in light of the attached claims and their equivalents.

What is claimed is:

1. A method, comprising:
   providing a mixture including at least one saturated alkyl tosylate and an alkyl Grignard reagent; and
   reacting the at least one saturated alkyl tosylate with the alkyl Grignard reagent in a C—C coupling reaction mechanism in the presence of a copper-containing catalyst to form a branched aliphatic alcohol.

2. The method of claim 1, wherein the step of reacting proceeds to a yield of at least 30% completion to form the branched aliphatic alcohol.

3. The method of claim 1, wherein the step of reacting proceeds to a yield of at least 40% completion to form the branched aliphatic alcohol.

4. The method of claim 1, wherein the step of reacting proceeds to a yield of at least 50% completion to form the branched aliphatic alcohol.

5. The method of claim 1, wherein the copper-containing catalyst comprises at least one of: $CuCl_2$, CuCl, CuI, CuBr, $CuBr.SMe_2$, or combinations thereof.

6. The method of claim 1, wherein the step of reacting is conducted in a solvent selected from: dimethylacetamide (DMAc), toluene, tetrahydrofuran (THF), dimethylformamide (DMF), benzotrifluoride, hexafluoroisopropanol (HFIP), 1,2-dichloroethane (DCE), dimethoxyethane (DME), hexafluorobenzene, 1,4-dioxane, mesitylene, chlorobenzene, p-xylene, o-dichlorobenzene, 1,2,4-trichlorobenzene, 1-chloronaphthalene, or combinations thereof.

7. The method of claim 1, wherein the mixture further includes at least one of an additive or a ligand.

8. The method of claim 1, wherein the at least one saturated alkyl tosylate is formed by reacting an alcohol with a tosyl-containing compound.

9. The method of claim 1, wherein the step of reacting occurs at a temperature in a range of 0° C. to −100° C.

10. The method of claim 1, wherein the alkyl Grignard reagent comprises an alcohol with a protecting group selected from: p-methoxybenzyl alcohol (PMB), tetrahydropyran (THP), or combinations thereof.

11. The method of claim 2, wherein the copper-containing catalyst comprises at least one of: $CuCl_2$, CuCl, CuI, CuBr, $CuBr.SMe_2$, or combinations thereof.

12. The method of claim 2, wherein the step of reacting occurs at a temperature in a range of 0° C. to −100° C.

13. The method of claim 2, wherein the alkyl Grignard reagent comprises an alcohol with a protecting group selected from: p-methoxybenzyl alcohol (PMB), tetrahydropyran (THP), or combinations thereof.

14. The method of claim 1, wherein the copper-containing catalyst comprises copper(I).

15. The method of claim 1, wherein the copper-containing catalyst comprises copper(II).

16. The method of claim 1, wherein the at least one saturated alkyl tosylate is a branched saturated alkyl tosylate.

17. The method of claim 7, wherein the additive is LiCl or LiOMe.

18. The method of claim 7, wherein the ligand is N-methyl-2-pyrrolidone (NMP), prop-1-yn-1-ylbenzene, or tetramethylethylenediamine (TMEDA).

19. The method of claim 1, wherein the copper-containing catalyst is $CuBr.SMe_2$.

20. The method of claim 6, wherein the step of reacting is conducted in THF.

* * * * *